United States Patent
Camblor Fernandez et al.

(10) Patent No.: US 6,500,404 B1
(45) Date of Patent: *Dec. 31, 2002

(54) ZEOLITE ITQ-3

(75) Inventors: Miguel-Angel Camblor Fernandez, Valencia (ES); Avelino Corma Canos, Valencia (ES); Luis-Angel Villaescusa Alonso, Valencia (ES)

(73) Assignees: Consejo Superior de Investigacones Cientificas, Madrid (ES); Universidad Politecnica de Valencia, Valencia (ES)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/424,897
(22) PCT Filed: May 29, 1998
(86) PCT No.: PCT/ES98/00155
§ 371 (c)(1), (2), (4) Date: Feb. 28, 2000
(87) PCT Pub. No.: WO98/54091
PCT Pub. Date: Dec. 3, 1998

(30) Foreign Application Priority Data

May 31, 1997 (ES) ............................................... 9701229

(51) Int. Cl.$^7$ .......................... C01B 39/48; B01J 29/70; C07C 7/13; C07C 4/00; C10G 11/05
(52) U.S. Cl. ........................ 423/706; 423/709; 423/718; 423/335; 208/120.01; 208/130; 208/135; 208/310 Z; 585/639; 585/640; 585/648; 585/649; 585/650
(58) Field of Search .................................. 423/706, 709, 423/718, 335

(56) References Cited

U.S. PATENT DOCUMENTS

| | | | | |
|---|---|---|---|---|
| 4,076,842 A | * | 2/1978 | Plank et al. | |
| 5,268,161 A | * | 12/1993 | Nagagawa | 423/702 |
| 5,614,166 A | * | 3/1997 | Gies et al. | 423/718 |
| 5,939,044 A | * | 8/1999 | Nakagawa et al. | 423/706 |

FOREIGN PATENT DOCUMENTS

| WO | WO91/11258 | 8/1991 |
|---|---|---|
| WO | WO94/08899 | 4/1994 |

OTHER PUBLICATIONS

Cullity, Elements Of X–ray Diffraction, p. 511, 1978.*
Paul Wagner et al, Guest/Host Relationships in the Synthesis of the Novel Cage–Based Zeolites SSZ–35 SSZ–36, and SSZ–39, J. Am. Chem. Soc. 2000. 122, 263–273.
Camblor et al., Dec. 1997, Angew. Chem. Int. Ed. Engl. 36:2659–2611.

* cited by examiner

*Primary Examiner*—David Sample
(74) *Attorney, Agent, or Firm*—Klauber & Jackson

(57) ABSTRACT

The present invention refers to a crystalline material of zeolitic nature named ITQ-3 characterized by its characteristic X-ray diffraction pattern and its microporous properties, to the process of preparation thereof characterized by the use of one or several organic additives in a reaction mixture that is made to crystallize by heating and to the use thereof in processes of separation and transformation of organic compounds, which material has the empirical formula $x(M_{1/n}XO_2):yYO_2:SiO_2$ where x has a value lower than 0.15 and may be equal to zero; and y has a value lower than 0.1 and may be equal to zero; M is $H^+$ or an inorganic cation of charge +n, X is a chemical element with oxidation state (Al, Ge, B and Cr), Y is a chemical element with oxidation state (Ti, Ge and V), and when x=0 and y=0 can be described as a new polymorphous of silica of microporous nature.

62 Claims, No Drawings

ZEOLITE ITQ-3

TECHNICAL FIELD

Microporous Crystalline Materials

BACKGROUND

Zeolites are microporous crystalline materials of variable composition characterized by a $TO_4$ tetrahydra crystalline lattice (wherein T represents atoms in the formal oxidation state of +3 or +4, such as for example Si, Ti, Al, Ge, B, Ga 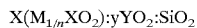 which all share their vertexes giving rise to a three-dimensional structure containing channels and/or cavities of molecular dimensions. When some of the atoms T have an oxidation state lower than +4, the crystalline lattice formed has negative charges which are compensated by the presence of organic or inorganic cations in the channels or cavities. Organic molecules and $H_2O$ can also be located in these channels and cavities, so in general, the chemical composition of zeolites can be represented by the following empirical formula:

$$X(M_{1/n}XO_2):yYO_2:SiO_2$$

wherein M is one or several organic or inorganic cations with charge +n; X is one or several trivalent elements; Y is one or several tetravalent elements, generally Si; and R is one or several organic substances. Although the nature of M, X, Y and R and the values of x, y, z and w can, in general, be varied by means of post-synthesis treatments, the chemical composition of a zeolite (just as it is synthesized or after calcination thereof) has a range characteristic of each zeolite and its preparation method.

On the other hand, a zeolite is also characterized by its crystalline structure, which defines a system of channels and cavities and gives rise to a specific X-ray diffraction pattern. In this way, zeolites are differentiated from each other by their range of chemical composition plus their X-ray diffraction pattern. Both characteristics (crystalline structure and chemical composition) also determine the physico-chemical properties of each zeolite and the applicability thereof in different industrial processes.

DESCRIPTION OF THE INVENTION

The present invention refers to a microporous crystalline material of zeolitic nature named ITQ-3, 5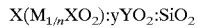 its method of obtainment and to its applications.

The material is characterized by its chemical composition and its X-ray diffraction pattern. In its anhydrous and calcined formed, the chemical composition of ITQ-3 may be represented by the empirical formula:

$$X(M_{1/n}XO_2):yYO_2:SiO_2$$

wherein x has a value lower than 0.15; it may be equal to zero; and y has a value lower than 0, 1; it may be equal to zero; M is $H^+$ or an inorganic cation of charge +n; X is a chemical element with oxidation state (Al, Ge, B, Cr) and Y is a chemical element with oxidation state +4 (Ti, Ge, V), when x=0 and y=0 the material can be described as a new polymorphous of silica of microporous nature. In the preferred embodiment of the present invention, ITQ-3 has the composition, in a calcined and anhydrous state $$x(HXO_2):SiO_2$$

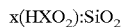

wherein X is a trivalent element and x has a value lower than 0.1 and may be equal to zero, in which case the material may be described by means of the formula $SiO_2$. However, it is possible, in terms of the synthesis method and the calcination or subsequent treatments, the existence of defects in the crystalline lattice, manifested by the presence of Si—OH groups (silanols). These defects have not been included in the above empirical formulae. In a preferred embodiment of the present invention, ITQ-3 has a very low concentration of this type of defect (silanol concentration lower than 15% with respect to the total Si atoms, preferably lower than 6%, measured by nuclear magnetic resonance spectroscopy of $^{29}Si$ in spinning angle).

The X-ray diffraction pattern of ITQ-3 just as it is synthesized as obtained by the powder method using a variable divergence slit and the Cu $K\alpha$ radiation, is characterized by the following values of $2^{\theta}$ angles and relative intensities ($I/I_o$):

TABLE I

| $2\theta$ (°) | $I/I_o$ (%) |
|---|---|
| 8.54 | 100 |
| 9.28 | 85 |
| 10.07 | 15 |
| 11.04 | 5 |
| 12.41 | 5 |
| 13.60 | 7 |
| 14.17 | 3 |
| 15.70 | 14 |
| 17.02 | 11 |
| 17.58 | 15 |
| 18.10 | 85 |
| 18.84 | 20 |
| 19.29 | 30 |
| 19.56 | 30 |
| 20.20 | 65 |
| 20.35 | 70 |
| 20.94 | 25 |
| 22.08 | 5 |
| 22.25 | 5 |
| 22.93 | 5 |
| 23.21 | 5 |
| 23.73 | 60 |
| 23.90 | 20 |
| 24.07 | 35 |
| 24.11 | 25 |
| 24.47 | 25 |
| 25.04 | 90 |
| 25.49 | 45 |
| 26.12 | 10 |
| 26.63 | 8 |
| 27.14 | 10 |
| 27.83 | 10 |
| 28.23 | 10 |
| 28.85 | 10 |
| 29.08 | 10 |
| 30.33 | 20 |
| 31.53 | 25 |
| 32.43 | 15 |
| 32.84 | 20 |
| 34.37 | 5 |

The positions and relative intensities of the peaks depend to a certain degree on the chemical composition of the material (the pattern represented in Table I refers to the material whose lattice is exclusively comprised of silicon oxide, $SiO_2$ and synthesized using a quaternary ammonium cation as a structure-directing agent). The relative intensities may also be affected by phenomena of preferred orientation of the crystals, produced during preparation of the sample, while the precision in the interplanar spacing measurement depends on the quality of alignment of the goniometer. Moreover, calcination can yield significant changes in the X-ray diffraction pattern, due to the removal of organic compounds retained during synthesis in the zeolite pores, so that Table II represents the X-ray diffraction pattern of ITQ-3 of calcined ITQ-3 of composition $SiO_2$ is represented:

TABLE II

| 2θ | I/I$_o$ (%) |
|---|---|
| 8.66 | 100 |
| 9.10 | 82 |
| 10.14 | 32 |
| 11.08 | 4 |
| 12.51 | 6 |
| 15.87 | 4 |
| 16.93 | 6 |
| 17.26 | 5 |
| 17.81 | 7 |
| 18.27 | 46 |
| 18.81 | 9 |
| 19.51 | 17 |
| 20.10 | 21 |
| 20.38 | 11 |
| 20.74 | 10 |
| 22.17 | 9 |
| 22.26 | 8 |
| 23.90 | 9 |
| 24.04 | 12 |
| 24.17 | 15 |
| 24.27 | 11 |
| 24.42 | 10 |
| 24.84 | 10 |
| 25.12 | 40 |
| 25.52 | 7 |
| 25.62 | 7 |
| 27.23 | 8 |
| 27.53 | 5 |
| 27.91 | 4 |
| 28.12 | 4 |
| 28.27 | 5 |
| 28.48 | 4 |
| 28.67 | 6 |
| 30.54 | 10 |
| 30.83 | 6 |
| 31.13 | 7 |
| 31.79 | 13 |
| 32.48 | 6 |
| 32.84 | 4 |
| 33.06 | 8 |
| 33.46 | 3 |
| 33.48 | 3 |
| 34.15 | 4 |
| 34.26 | 4 |
| 34.64 | 3 |
| 34.77 | 3 |

The present invention also refers to the method of preparation of ITQ-3. This comprises thermal treatment at temperatures between 80 and 200° C., preferably between 130 and 180° C., of a reaction mixture that contains a source of $SiO_2$ (such as, for example, tetraethylorthosilicate, colloidal silica, amorphous silica), an organic cation in hydroxide form, preferably N,N-dimethyl-6-azonium-1,3,3-trimethylbicyclo(3.2.1)octane (I) hydroxide, hydrofluoric acid and water. Alternatively, it is possible to use the organic cation as a salt (for example, a halide, preferably chloride) and to substitute hydrofluoric acid by a fluoride salt, preferably $NH_4F$. The reaction mixture is characterized by its relatively low ph<12, preferably<11, and which may also be neutral or slightly acidic.

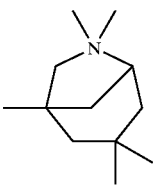

I

Optionally, it is possible to add a source of another tetravalent element Y and/or trivalent element X, preferably Ti or Al. The addition of this element may be done before heating the reaction mixture or in an intermediate time during said heating. Occasionally, it may be convenient to add also in a certain time during the preparation of ITQ-3 crystals (up to 15% by weight with respect to the total inorganic oxides, preferably up to 10% by weight) as cryst6allizer promoters (seeding). The composition of the reaction mixture in oxide form responds to the general formula $$RR_2O:aHF:xHXO_2:yYO_2:SiO_2:wH_2O$$

wherein X is one or several trivalent elements, preferably Al; Y is one or several tetravalent elements; R is an organic cation, preferably N,N-dimethyl-6-azonium-1,3,-trimethyl-6-bicyclo(3.2.1.)octane, and the values of r,a,x,y and w are in the ranges R=0.05–1.0, preferably 0.1–0–75
A=0–1.5, preferably 0.1–1.5
X=0–0.15
Y=0–0.1
W=3–100, preferably 5–50, more preferably 7–50

The thermal treatment of the reaction mixture may be done in static or with stirring of the mixture. Once the crystallization is finished the solid product is separated and dried. Subsequent calcination at temperatures between 400 and 650° C., preferably between 450 and 600° C., produces the decomposition of the organic residue occluded in the zeolite and renders the free zeolitic channels.

This method of synthesis of ITQ-3 zeolite has the peculiarity that it does not require introduction of alkali cations in the reaction medium. As a consequence the organic cation R is the only cation that balances the lattice charges when the zeolite contains a trivalent element in its crystalline lattice. Therefore, simple calcination to decompose the organic cation leaves the zeolite in acid form, without the need to resort to cation exchange processes. Besides, the absence of alkali cations in the reaction mixture allows synthesis of the material containing elements such as Ti(IV), which would not be possible to introduced in the lattice in the presence of these cations (see, for example, M. A. Camblor, A. Corma, J. Pérez-Pariente, Zeolites, vol. 13, 82–87, 1993). Thus, once calcined the material has the general formula $$X(HXO_2):yYO_2:SiO_2$$

wherein x is lower than 0.15, and may be equal to 0; y is lower than 0.1, and may also be zero; X is a chemical element with oxidation state of +3 and Y is a chemical element with an oxidation state of +4.

The crystalline material of the present invention may be used in several applications, such as, for example, in processes for the separation of linear and branched paraffin compounds. Hence, a mixture of isobutane and n-butane or isopentane and n-pentane may be enriched in the more branched isomer by selective adsorption of the linear paraffin by the microporous material of the present invention. Said material is particularly suitable for use in this type of process due to its high adsorption capacity (micropore volume determined by adsorption of $N_2$=0.23 cm$^3$/g) and its small pore size (maximum opening ≦5.5 Å, determined by adsorption of Ar, using the Horvath-Kawazoe formalism).

Likewise and preferably using the pure silica polymorph, it is possible to separate by selective adsorption the n-olefins of mixtures containing normal and isoolefins, enriching the final stream in isoolefins. In general, this material would allow the separation of organic compounds, which may or may not contain heteroatoms, with sizes smaller than 5–5.5 Å present in mixtures also containing organic compounds of larger sizes. Due to the hydrophobic characteristics of the silica polymorph, ITQ-3 would permit selective adsorption of organic compounds with kinetic diameter smaller than 5–5.5 Å present in polar media, such as, for example, in aqueous media.

From the view point of its use as a catalyst, this material, when prepared in the acid form and which may or may not contain supported transition metals such as Pt, Pd or Ni, allows the selective cracking and hydrocracking of linear alkanes with respect to the branched ones or to larger hydrocarbons, thus being adequate as a catalyst or catalytic cracking additive and as a catalyst in the "selectoforming" type process that involves hydrocracking of the stream coming from the reformed unit for the purpose of removing n-paraffins.

Likewise, ITQ-3 gives good results as an alkane and alkene catalyst for the purpose of producing high yields of ethylene, propylene and butene, thus being suitable as a catalyst for production processes of short olefins by catalytic steam cracking. Moreover, its possibilities of selectively cracking linear paraffins makes it a good catalyst for dewaxing processes. Finally, this material is a good catalyst in processes of transformation of methanol into olefins.

EXAMPLES

Example 1

This example illustrates the preparation of N,N-dimethyl-6-azonium-1,3,3-trimethylbicyclo(3.2.1.)octane hydroxide.

38.32 of 1,3,3-trimethyl-6-azabicyclo (3.2.1.)octane (Aldrich), 220 g of ChCl$_3$ (SDS synthesis grade) and 82.50 g of potassium carbonate sesquihydrate (99%, Aldrich) are introduced in a 500 ml flask. To this mixture 31 ml of $CH_3I$ (99% Aldrich) are added dropwise and under stirring in an ice bath. After seven days of stirring at room temperature the mixture is filtered and the liquid is evaporated in a rotovap. After washing the obtained solid with ethyl acetate and drying it, 71.37 g of a solid is obtained, whose nuclear magnetic resonance spectrum in $CDCl_3$ indicates that it is a nucleophilic substitution product, namely, the iodide of the organic cation corresponding to the dimethylation of the amine. Chemical analysis of the product 45.5% C, 4.42% N, 7.54% H, Theoretical: 46.51% C, 4.53% N, 7.82% H) confirms this result.

The hydroxide form of the structure-directing agent is obtained by anion exchange using Dowex 1 (Sigma) resin, previously washed with distilled water until pH=7. To a solution of 9.27 g of the former product in 194.02 g of water, 221.73 g of resin were added and left under stirring for about 12 hours. After filtering the resin, the solution was titrated with HCl (aq) using phenolphthalein as indicator, and finding an efficiency of 96.62% in the exchange. This solution could be concentrated in the rotovap for use in the synthesis of ITQ-3, and its final concentration is obtained by means of further titration.

Example 2

This example illustrates the preparation of pure silica ITQ-3, using N,N-dimethyl-6-azonium-1,3,3-trimethylbicyclo(3.2.1.)octane hydroxide as the organic structure-directing agent.

12.08 g. Of tetraethylorthosilicate (TEOS) were added to 23.02 g. Of a solution containing 1.26 moles of N,N-dimethyl-6-azonium-1,3,3-trimethylbicyclo(3.2.1.)octane hydroxide per 1000 g, obtained in the way described in Example 1, and the mixture was stirred, allowing evaporation of the ethanol produced in the hydrolysis of TEOS, along with some water. After 6 hours of stirring (weight loss: 18.99 g) 0.57 g of water and 1.21 g. Of HF (aq) (48% Aldrich) were added. The paste obtained is introduced in a polytetrafluoroethylene lined autoclave and kept at 150° C. under rotation (60 rpm) for 19 days. Then, the autoclave was cooled down, the contents were filtered and the solid washed with water and dried at 100° C. Its X-ray diffraction pattern is shown in Table 1. After calcination at 580° C. the white solid obtained has the diffractogram of Table 2. Chemical analysis by atomic absorption spectroscopy of the calcined material reveals that, within the detection limits of the technique and the experimental error, the obtained product is silica ($SiO_2$). $^{29}$Si MAS NMR spectroscopy measurements indicate that the calcined material contains a very low proportion of connectivity defects, as inferred from the ratio of SiOH to total Si (calculated as the quotient between the area of the peak centered at ※101 ppm and the total area of all of the peaks). $N_2$ adsorption measures indicate a surface area of 455 m$^2$/g (B.E.T. method) and a micropore volume of 0.23 cc/g. The solid state $^{13}$NMR spectrum of the material just as it was made clearly shows the presence of the organic cation occluded in the inorganic crystalline lattice, as well as the elemental analysis which gives molar ratios are practically those of the organic cation (C/N=11.8, H/N=23.4).

Examples 3–6

These examples illustrate the preparation of pure silica of Al-containing ITQ-3, whether in the presence or absence of seeds.

The same experimental procedure of example 2 was followed. The synthesis conditions are listed in Table 3. In examples 4 and 5 metal aluminum and aluminum nitrate nonahydrate were used, respectively, as an aluminum source. The OH$_{ef}$ formalism is defined as the difference between the added OH moles and those employed by the aluminum to reach tetrahydral coordination. All the crystallizations were carried out under stirring (60 r.p.m.). In all cases high crystallinity ITQ-3 was obtained.

TABLE III

| | Molar ratios | | | | | | | |
|---|---|---|---|---|---|---|---|---|
| example | $SiO_2$/$Al_2O_3$ | T/$SiO_2$ | OH$_{ef}$/F | $H_2O$/$SiO_2$ | seeds % ($SiO_2$) | T(° C.) | t (days) | Si/Al (solid) |
| 3 | | 0.48 | 1 | 14.6 | 2.7 | 135 | 14 | |
| 4 | 60 | 0.52 | 1 | 15 | — | 150 | 35 | 38.8 |

TABLE III-continued

| | Molar ratios | | | | | | | |
|---|---|---|---|---|---|---|---|---|
| example | SiO$_2$/Al$_2$O$_3$ | T/SiO$_2$ | OH$_{ef}$/F | H$_2$O/SiO$_2$ | seeds % (SiO$_2$) | T(° C.) | t (days) | Si/Al (solid) |
| 5 | 104 | 0.55 | 1 | 17.4 | 4.7 | 135 | 14 | 55.8 |
| 6 | 53 | 0.69 | 1 | 16.5 | 4.7 | 135 | 13 | 32.7 |

What is claimed is:

1. A microporous crystalline material of zeolitic nature with an X-ray diffraction pattern substantially in accordance with Tables I and II for the material as synthesized and after calcination, respectively, and with a chemical composition in the calcined and anhydrous state represented by an empirical formula $$x(M_{1/n}XO_2):yYO_2:SiO_2$$

wherein x has a value lower than 0.15; y has a value lower than 0.1; M is H$^+$ or an inorganic cation of charge +n; X, when present, is a chemical element with oxidation state +3 being at least one of Al, Ge, B and Cr; and Y, when present, is a chemical element with oxidation state +4 being at least one of Ti, Ge and V.

2. A crystalline material according to claim 1 having a chemical composition in the calcined and anhydrous state represented by the empirical formula $$x(HXO_2):yYO_2:SiO_2$$

wherein X, when present, is a trivalent element being at least one of Al, B, Ga, and Cr; Y, when present, is a tetravalent element different from Si and being at least one of Ti, Ge and V; x has a value lower than 0.15, y has a value lower than 0.1, and wherein the cation H$^+$ may be exchanged by other mono-, di- or trivalent organic or inorganic cations.

3. A crystalline material in accordance with claim 1 having a chemical composition in the calcined and anhydrous state represented by the empirical formula $$x(HAlO_2):SiO_2$$

wherein x has a value lower than 0.15 and may also be equal to zero and wherein the H$^+$ cation may be exchanged by other mono-, di- or trivalent organic or inorganic cations.

4. A crystalline material in accordance with claim 1 having a chemical composition in the calcined and anhydrous state represented by the formula SiO$_2$.

5. A method of using the microporous crystalline material of claim 1 in a process of separation of iso- and normal paraffins, the method comprising adding a suitable amount of the material and selectively adsorbing the normal paraffins to the material.

6. A method of using the microporous crystalline material of claim 1 in a process of separation of isobutane and n-butane, the method comprising adding a suitable amount of the material and selectively adsorbing n-butane to the material.

7. A method of using the microporous crystalline material of claim 1 in a process of separation of isopentane and n-pentane, the method comprising adding a suitable amount of the material and selectively adsorbing n-pentane to the material.

8. A method of using the microporous crystalline material of claim 1 in processes of separation of iso and normal olefins, the method comprising adding a suitable amount of the material and selectively adsorbing n-olefins to the material.

9. A method of using the microporous crystalline material of claim 1 in a process of separation of isobutene and normal butene, the method comprising adding a suitable amount of the material and selectively adsorbing n-butene to the material.

10. A method of using the microporous crystalline material of claim 1 in a process of separation of isopentene and normal pentene, the method comprising adding a suitable amount of the material and selectively adsorbing n-pentene to the material.

11. A method of using the microporous material of claim 1, in a process of separation of organic compounds, selected from organic compounds comprising heteroatoms, organic compounds not comprising heteroatoms and mixtures thereof, the organic compounds having a kinetic diameter smaller than 5–5.5 Å, the method comprising adding a suitable amount of the material and selectively adsorbing to the material the organic compounds having kinetic diameters smaller than 5–5.5 Å from mixtures containing compounds with a kinetic diameter larger than 5–5.5 Å.

12. A method of using the microporous crystalline material of claim 1 in a process of separation of organic compounds with a kinetic diameter smaller than 5.5 Å from polar streams, for the purpose of purifying said streams, the method comprising adding a suitable amount of the material to said stream and selectively adsorbing the organic compounds to the material.

13. A method according to claim 12, wherein the polar stream is an aqueous polar stream.

14. A method of using the microporous crystalline material of claim 1 as a catalyst in a process of selective cracking and hydrocracking of linear paraffins, linear olefins and mixtures thereof, the method comprising contacting the linear paraffins with a suitable amount of the material.

15. A method of using the microporous crystalline material of claim 1 as a "post-reformate" catalyst in a process for post-reformation of gasoline, the method comprising contacting the gasoline being subject to reformation, with a suitable amount of the material.

16. A method of using the microporous crystalline material of claim 1, in a catalytic steam cracking process to produce a stream with a high content of ethylene, propylene and butene by cracking an initial stream of alkanes and alkenes, the method comprising contacting said initial stream with a suitable amount, whereby the material is used as a catalyst.

17. A method of using the microporous crystalline material of claim 1 as a catalyst in a dewaxing process by selective cracking of n-paraffins, the method comprising contacting the n-paraffins with a suitable amount of the material.

18. A method of using the microporous crystalline material of claim 1 as a catalyst in processes of conversion of methanol into olefins, the method comprising contacting the methanol with a suitable amount of the material.

19. A method of using the microporous crystalline material of claim 1, in a catalytic cracking process to produce a stream with a high content of ethylene, propylene and butene by cracking an initial stream of alkanes and alkenes, the method comprising contacting said initial stream with a suitable amount, whereby the material is used as a catalyst.

20. A process for synthesizing a crystalline material of zeolitic nature with an X-ray diffraction pattern substantially in accordance with Tables I and II for the material as synthesized and after calcination, respectively, and with a chemical composition in the calcined and anhydrous state represented by an empirical formula $$x(M_{1/n}XO_2):yYO_2:SiO_2$$

wherein x has a value lower than 0.15; y has a value lower than 0.1; M is $H^+$ or an inorganic cation of charge +n; X, when present, is a chemical element with oxidation state +3 being at least one of Al, Ge, B and Cr and Y, when present, is a chemical element with oxidation state +4 being at least one of Ti, Ge and V, wherein a reaction mixture that contains a source of $SiO_2$, an organic cation $R^+$ being N,N-dimethyl-6-azonium-1,3,3-trimethylbicyclo(3.2.1.)octane, a source of F, a source, when present, of one or several tetravalent elements Y different from Si, a source, when present, of one or several tetravalent elements X, and water, is subjected to heating at a temperature between 80 and 200° C. until achieving crystallization thereof and wherein the reaction mixture has a composition, in terms of molar ratios of oxides, of $X_2O_3/SiO_2=0-0.1$, $ROH/SiO_2=0.05-2.0$,
$F/Si=0.2-1.5$,
$YO_2/SiO_2=0-0.1$
$H_2O/SiO_2=3-100$.

21. A process according to claim 20, wherein the reaction mixture does not comprise a source of a tetravalent element other than Si, and has a composition in terms of molar ratios of oxides, of $X_2O_3/SiO_2=0-0.1$, $ROH/SiO_2=0.05-2.0$, $F^-/Si=0-2$, and $H_2O/SiO_2=3-100$.

22. A process according to claim 21, wherein the reaction mixture has a composition in terms of molar ratios of oxides, of
$X_2O_3/SiO_2=0-0.05$
$ROH/SiO_2=0.2-1.5$
$F^-/Si=0.2-1.5$
$H_2O/SiO_2=5-50$.

23. A process according to claim 21, wherein the reaction mixture has a composition in terms of molar ratios of oxides, of
$X_2O_3/SiO_2=0-0.05$
$ROH/SiO_2=0.2-1.5$
$F^-/Si=0.2-1.5$
$H_2O/SiO_2=7-50$.

24. A process according to claim 21, wherein the reaction mixture does not comprise a source of a tetravalent element other than Si, $X_2O_3$ is $Al_2O_3$, and the reaction mixture has a composition, in terms of molar ratios of oxides, of $Al_2O_3/SiO_2=0-0.1$, $ROH/SiO_2=0.05-2.0$, $F^-/Si=0-2$, and $H_2O/SiO_2=3-100$.

25. A process according to claim 24, wherein the reaction mixture has a composition, in terms of molar ratio of oxides, of
$Al_2O_3/SiO_2=0-0.05$
$ROH/SiO_2=0.2-1.5$
$F^-/Si=0.2-1.5$
$H_2O/SiO_2=7-50$.

26. A process according to claim 20, wherein the reaction mixture does not comprise a source of a tetravalent element other than Si, does not comprise a source of a trivalent element, and has a composition, in terms of molar ratios of oxides, of $ROH/SiO_2=0.05-2-0$, $F^-/Si=0-2$, and $H_2O/SiO_2=3-100$.

27. A process according to claim 26, wherein the reaction mixture has a composition, in terms of molar ratios of oxides, of
$Al_2O_3/SiO_2=0-0.05$
$ROH/SiO_2=0.2-1.5$
$F^-/Si=0.2-1.5$
$H_2O/SiO_2=5-50$.

28. A process according claim 26, wherein the reaction mixture has a composition, in terms of molar ratios of oxides, of
$ROH/SiO_2=0.2-1.5$
$F/Si=0.2-1.50$
$H_2O/SiO_2=5-50$.

29. A process according to claim 26, wherein the reaction mixture has a composition, in terms of molar ratios of oxides, of
$ROH/SiO_2=0.2-1.5$
$F^-/Si=0.2-1.50$
$H_2O/SiO_2=7-50$.

30. A process according to claim 20, wherein the reaction mixture does not comprise a source of a trivalent element and has a composition, in terms of molar ratios of oxides, of
$ROH/SiO_2=0.05-2.0$,
$F^-/Si=0-2$, $YO_2/SiO_2=0-4.1$, and
$H_2O/SiO_2=3-100$.

31. A process according to claim 30, wherein the reaction mixture has a composition, in terms of molar ratios of oxides, of
$ROH/SiO_2=0.2-1.5$
$F^-/Si=0.2-1.50$
$YO_2/SiO_2=0-0.1$
$H_2O/SiO_2=5-50$.

32. A process according to claim 30, wherein the reaction mixture has a composition, in terms of molar ratios of oxides, of
$ROH/SiO_2=0.2-1.5$
$F^-/Si=0.2-1.5$
$YO_2/SiO_2=0-0.1$
$H_2F/SiO_2=7-50$.

33. A process according to claim 20, wherein the organic cation is selected from N,N-dimethyl-6-azonium-1,3,3-trimethylbicyclo(3.2.1.)octane hydroxide, N,N-dimethyl-6-azonium-1,3,3-trimethylbicyclo(3.2.1.)octane salt, and mixtures thereof, and the fluoride anion is added in the form of ammonium fluoride, such that reaction mixture achieves a pH from slightly acidic to 12.

34. A process according to claim 33, wherein the pH of the reaction mixture is from slightly acidic to 11.

35. A process according to claim 20, wherein to the reaction mixture is added an amount of crystalline material as crystallization promoter, said amount being 0.05 to 15% by weight with regard to the total silica added.

36. A process according to claim 35, herein the amount of crystalline material added as crystallization promoter is comprised in the range of 0.05 to 5% by weight with regard to the total silica added.

37. A process according to claim 20, wherein the reaction mixture is essentially free of alkali cations, the only limitation being a possible content of alkali impurities of reactants used.

38. A process according to claim 20, wherein a source of a tetravalent element different than Si is added or a trivalent element is added in an intermediate step during heating of the reaction mixture.

39. A process according to claim 20, wherein the reaction mixture is subjected to heating at a temperature between 130 and 180° C.

40. A process according to claim 20, wherein the reaction mixture has a composition, in terms of molar ratios of oxides, of $X_2O_3/SiO_2=0-0.5$
$ROH/SiO_2=0.2-1.50$
$F^-/Si=0.2-1.50$
$YO_2/SiO_2=0-0.1$.
$H_2O/SiO_2=5-50$.

41. A process according to claim 20, wherein the reaction mixture has a composition, in terms of molar ratios of oxides, of $X_2O_3/SiO_2=0-0.5$
$ROH/SiO_2=0.2-1.50$
$F^-/Si=0.2-1.50$
$YO_2/SiO_2=0-0.1$
$H_2O/SiO_2=7-50$.

42. A process according to claim 20, wherein the source of the tetravalent element different from Si is added in an intermediate step during heating of the reaction mixture.

43. A process according to claim 20, wherein the source of the trivalent element is added in an intermediate step during heating of the reaction mixture.

44. A microporous crystalline material of zeolitic nature with an X-ray diffraction pattern substantially in accordance with Tables I and II for the material as synthesized and after calcination, respectively, and with a chemical composition in the calcined and anhydrous state represented by an empirical formula

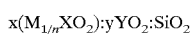
$x(M_{1/n}XO_2):yYO_2:SiO_2$ wherein x has a value lower than 0.15; y has a value lower than 0.1; M is H+ or an inorganic cation of charge +n; X, when present, is a chemical element with oxidation state +3 being at least one of Al, Ge, B and Cr and Y, when present, is a chemical element with oxidation state +4 being at least one of Ti, Ge and V, and wherein the crystalline material has been obtained from a reaction mixture comprising a source of F–.

45. A crystalline material according to claim 44 having a chemical composition in the calcined and anhydrous state represented by the empirical formula

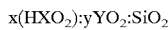
$x(HXO_2):yYO_2:SiO_2$ wherein X, when present, is a trivalent element being at least one of Al, B, Ga and Cr; Y, when present, is a tetravalent element different from Si being at least one of Ti, Ge and V, x has a value lower than 0.15, y has a value lower than 0.1, and wherein the cation H+ may be exchanged by other mono-, di- or trivalent organic or inorganic cations.

46. A crystalline material in accordance with claim 44 having a chemical composition in the calcined and anhydrous state represented by the empirical formula

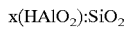
$x(HAlO_2):SiO_2$ wherein x has a value lower than 0.15 and may also be equal to zero and wherein the H+ cation may be exchanged by other mono-, di- or trivalent organic or inorganic cations.

47. A crystalline material in accordance with claim 44 having a chemical composition in the calcined and anhydrous state represented by the formula $SiO_2$.

48. A method of using the microporous crystalline material of claim 44, in a process of separation of iso- and normal paraffins, the method comprising adding a suitable amount of the material and selectively adsorbing the normal paraffins to the material.

49. A method of using the microporous crystalline material of claim 44, in a process of separation of isobutane and n-butane, the method comprising adding a suitable amount of the material and selectively adsorbing n-butane to the material.

50. A method of using the microporous crystalline material of claim 44, in a process of separation of isopentane and n-pentane, the method comprising adding a suitable amount of the material and selectively adsorbing n-pentane to the material.

51. A method of using the microporous crystalline material of claim 44, in processes of separation of iso- and normal olefins, the method comprising adding a suitable amount of the material and selectively adsorbing n-olefins to the material.

52. A method of using the microporous crystalline material of claim 44, in a process of separation of isobutene and normal butene, the method comprising adding a suitable amount of the material and selectively adsorbing n-butene to the material.

53. A method of using the microporous crystalline material of claim 44, in a process of separation of isopentene and normal pentene, the method comprising adding a suitable amount of the material and selectively adsorbing n-pentene to the material.

54. A method of using the microporous material of claim 44, in a process of separation of organic compounds, selected from organic compounds comprising heteroatoms, organic compounds not comprising heteroatoms and mixtures thereof, the organic compounds having a kinetic diameter smaller than 5–5.5 Å, the method comprising adding a suitable amount of the material and selectively adsorbing to the material the organic compounds having kinetic diameters smaller than 5–5.5 Å from mixtures containing compounds with a kinetic diameter larger than 5–5.5 Å.

55. A method of using the microporous crystalline material of claim 44, in a process of separation of organic compounds with a kinetic diameter smaller than 5.5 Å from polar streams, for the purpose of purifying said streams, the method comprising adding a suitable amount of the material to said stream and selectively absorbing the organic compounds to the material.

56. A method of using the microporous crystalline material of claim 44, as a catalyst in a process of selective cracking and hydrocracking of linear paraffins, linear olefins and mixtures thereof, the method comprising contacting the linear paraffins with a suitable amount of the material.

57. A method of using the microporous crystalline material of claim 44, as a "postreformate" catalyst in a process for postreformation of gasoline, the method comprising contacting the gasoline being subject to reformation, with a suitable amount of the material.

58. A method of using the microporous crystalline material of claim 44, in a catalytic steam cracking process to produce a stream with a high content of ethylene, propylene and butene by cracking an initial stream of alkanes and alkenes, the method comprising contacting said initial stream with a suitable amount of the material, whereby the material is used as a catalyst.

59. A method of using the microporous crystalline material of claim 44, as a catalyst in a dewaxing process by selective cracking of n-paraffins, the method comprising contacting the n-paraffins with a suitable amount of the material.

60. A method of using the microporous crystalline material of claim 44, as a catalyst in processes of conversion of methanol into olefins, the method comprising contacting the methanol with a suitable amount of the material.

61. A method of using the microporous crystalline material of claim 44, in a catalytic cracking process to produce a stream with a high content of ethylene, propylene and butene by cracking an initial stream of alkanes and alkenes, the method comprising contacting said initial stream with a suitable amount, whereby the material is used as a catalyst.

62. A microporous crystalline material of zeolitic nature with an X-ray diffraction pattern of Tables I and II for the material as synthesized and after calcination, respectively, and with a chemical composition in the calcined and anhydrous state represented by an empirical formula $$x(M_{1/n}/XO_2):yYO_2:SiO_2$$

wherein x has a value lower than 0.15; y has a value lower than 0.1; M is $H^+$ or an inorganic cation of charge +n; X, when present, is a chemical element with oxidation state +3 being at least one of Al, Ge, B and Cr and Y, when present, is a chemical element with oxidation state +4 being at least one of Ti, Ge and V.

* * * * *